United States Patent
Benne et al.

(10) Patent No.: US 9,102,006 B1
(45) Date of Patent: Aug. 11, 2015

(54) LIGHTED MANDREL FOR TRIMMING MEDICAL DEVICES

(71) Applicant: W. L. Gore & Associates, Inc., Newark, DE (US)

(72) Inventors: Jonathan G. Benne, Flagstaff, AZ (US); Jim L. Fields, Flagstaff, AZ (US); Gary M. Kesti, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 305 days.

(21) Appl. No.: 13/888,197

(22) Filed: May 6, 2013

Related U.S. Application Data (60) Provisional application No. 61/646,109, filed on May 11, 2012.

(51) Int. Cl.
  *B23K 26/36* (2014.01)
  *B23K 37/04* (2006.01)
  *B23K 26/00* (2014.01)

(52) U.S. Cl.
  CPC .............. *B23K 26/0066* (2013.01); *B23K 26/36* (2013.01); *B23K 37/04* (2013.01)

(58) Field of Classification Search
  CPC .................................. B23K 26/36; B23K 37/04
  USPC ............. 269/11, 47; 264/138, 154, 400, 40.1; 219/121.67, 121.68; 29/407.01, 407.04
  See application file for complete search history.

(56) References Cited

U.S. PATENT DOCUMENTS

| 4,436,979 | A |   | 3/1984  | Nilsen            |            |
|-----------|---|---|---------|-------------------|------------|
| 4,580,558 | A |   | 4/1986  | Cabrera et al.    |            |
| 4,749,840 | A | * | 6/1988  | Piwczyk           | 219/121.68 |
| 4,927,410 | A |   | 5/1990  | Kovacs            |            |
| 5,099,101 | A |   | 3/1992  | Millerick et al.  |            |
| 5,891,082 | A | * | 4/1999  | Leone et al.      | 604/21     |
| 5,997,570 | A | * | 12/1999 | Ligtenberg et al. | 607/92     |
| 6,696,666 | B2 |  | 2/2004  | Merdan et al.     |            |
| 7,812,941 | B2 |  | 10/2010 | Cameron et al.    |            |
| 2005/0182478 | A1 | | 8/2005 | Holman et al.     |            |
| 2005/0259863 | A1 | | 11/2005 | Freifeld         |            |
| 2010/0309307 | A1 | | 12/2010 | Jin              |            |
| 2011/0040394 | A1 | | 2/2011  | Park et al.      |            |
| 2011/0056350 | A1 | | 3/2011  | Gale et al.      |            |

FOREIGN PATENT DOCUMENTS

| DE | 19901530    | 7/2000 |
| JP | 10200270    | 7/1998 |
| WO | 2009-103815 | 8/2009 |

* cited by examiner

*Primary Examiner* — Samuel M Heinrich
(74) *Attorney, Agent, or Firm* — Gilbert R. Gabo (57) ABSTRACT

A medical device processing system is provided which includes a support wall having a support surface for supporting a medical device thereon, such as a graft device. The support wall is generally translucent to allow light to pass therethrough to illuminate a medical device supported on the support surface. The support wall can be formed from other suitable materials that are clear or at least translucent to allow light from a light emitting member to pass therethrough to illuminate the medical device. The support wall and/or the support surface can have any shape suitable to support and allow optimal transmission of light toward the medical device. The support wall can be generally tubular shaped to support tubular shaped medical devices, such as stent grafts.

23 Claims, 6 Drawing Sheets

LIGHTED MANDREL FOR TRIMMING MEDICAL DEVICES

CROSS REFERENCE TO RELATED APPLICATIONS

This application claims priority to U.S. Provisional Application No. 61/646,109, filed May 11, 2012. The disclosure of the prior application is considered part of and is incorporated by reference in the disclosure of this application.

BACKGROUND

1. Field

The present disclosure relates to the manufacture of medical devices and, more particularly, to a lighted mandrel used in the imaging, inspection, and trimming of medical devices.

2. Discussion of the Related Art

Systems for inspection, measurement and characterization of graft devices are generally known and disclosed in the art. It remains desirable, however, to provide a system that provides precise imaging and automated trimming of medical devices, such as grafts and stent grafts.

DETAILED DESCRIPTION OF THE ILLUSTRATED EMBODIMENTS

Persons skilled in the art will readily appreciate that various aspects of the present disclosure can be realized by any number of methods and systems configured to perform the intended functions. Stated differently, other methods and systems can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. Although the present disclosure can be described in connection with various principles and beliefs, the present disclosure should not be bound by theory.

In various embodiments, a medical device processing system is provided which includes a support wall having a support surface for supporting a medical device thereon, such as a graft device. The support wall is transparent or at least generally translucent to allow light to pass therethrough to illuminate a medical device supported on the support surface. In various embodiments, the support wall can be formed from suitable materials that are clear or at least translucent to allow sufficient transmission of light therethrough, such as quartz, silicon dioxide, sapphire, diamond, and ruby and other transparent crystals. The support wall and/or the support surface can have any shape suitable to support and allow optimal transmission of light toward the medical device. The support surface can be polished to maximize the transmission of light therethrough.

The medical device processing system, in accordance with various embodiments, can include a light emitting member which projects light through the support wall and toward and through the medical device to facilitate one or more processes, such as imaging, inspection, assembly, trimming, densification, surface treatments, etching, thermal treatments, or any combination thereof. In various embodiments, the light emitting member emits light substantially evenly across its entire translucent surface. In various embodiments, the light emitting member comprises a cold cathode fluorescent lamp (CCFL). Other types of lamps that can be used include fiber optic diffusers, LEDs, UV or IR lamps, or any other longitudinally extending light emitting source that emits a substantially uniform light outwardly therefrom.

In various embodiments, the medical device processing system can also include, for example, an imaging device, such as a digital camera, for capturing images of a medical device supported on the support wall; a cutting device, such as a laser or a blade, for cutting or trimming portions of a medical device supported on the support wall; and/or other desired suitable devices for processing a medical device.

Where a laser is used as the cutting device, the support wall should be of a material that: a) has low thermal conductivity; b) is transparent or translucent; and c) is not damaged by the heat required to cut the material.

The medical device processing system can include a controller, such as a computer, for controlling the imaging device and processing data therefrom. The controller can be operable to receive and process data from the imaging device to inform other processes of the medical device processing system. For example, one or a combination of the support wall, cutting device, or other components of the medical device processing system can be motorized and automatically actuated by the controller based on the data received by the imaging device and processed by the controller.

In various embodiments, the support wall forms a generally tubular shaped mandrel that extends along a longitudinal axis thereof. The mandrel includes a generally cylindrical outer surface on which a tubular-shaped medical device, such as an endovascular graft device, can be supported. The outer surface can be configured to constrain the graft device relative to the mandrel in one or both axial and rotational directions. The outer diameter of the outer surface can, for example, be sized to provide a friction fit between the graft device and the mandrel. Alternatively, it can be desirable to allow an air gap to exist between the medical device and the outer surface of the mandrel. For example, the mandrel can be grooved, hour-glass shaped or tapered or otherwise have reduced outer peripheral dimensions selectively along the mandrel to allow an air gap to exist between the medical device and the outer surface. Other suitable means can thus be used in conjunction with or as an alternative to a friction fit for constraining the graft device relative to the mandrel, such as a locating pin, edge or surface extending outwardly from the outer surface for engaging a particular edge or surface of the graft device.

In various embodiments, the support wall can include a generally cylindrical inner surface that defines a bore or lumen extending along the longitudinal axis for receiving and supporting a light-emitting member therein and forming a lighted mandrel. The support wall is clear or at least translucent to allow light from within the bore to pass therethrough toward the medical device to illuminate the medical device. A light emitting member, such as a rod-shaped cold cathode fluorescent lamp (CCFL), for example, can be placed into and supported in the bore of the mandrel for projecting light outwardly through the support wall and toward the medical device supported along the outer surface of the mandrel. Alternatively, in accordance with other embodiments, the support wall and light emitting member can be integrated. For example, the inner surface of the mandrel can be coated with a phosphor, such as zinc silicate or other halo phosphates; and the bore of the mandrel evacuated and filled with mercury vapor at low pressure. Electrodes can be placed at opposite ends of the mandrel for applying an electrical current to energize and ionize the mercury vapor and, in turn, cause a release of light from the phosphor coating along the inner surface of the mandrel and outward toward the medical device supported along the outer surface of the mandrel.

Medical devices can be formed from a variety of suitable materials known by those having ordinary skill in the art. Graft devices, for example, can include a graft wall formed from a fluoropolymer, such as expanded polytetrafluoroethylene (ePTFE). The graft wall, depending on the type of material, thickness of the material and density of the material will allow some degree of light transmission therethrough. The system can be operable to transmit a predetermined amount of light to provide light transmission through only certain portions of the graft device. A graft device, for example, may have a graft wall with varying thicknesses and/or densities and, therefore, varying degrees of translucence along the graft wall. In this case, the light emitting member, for example, can be specified, adjusted or otherwise variable to allow transmission of light through portions of the graft wall at or below a certain wall thickness or densities to facilitate inspection, measurement, imaging and/or trimming of certain features of the graft device.

Graft devices can also include non-translucent features, such as a metallic frame or stent, an anchor, a reinforcement, a radiopaque marker, or thickened or densified areas of the graft. Such non-translucent features tend to block light transmitted outwardly from the mandrel. Thus, from the viewpoint of an observer or imaging system, the translucent portions of the graft wall will appear illuminated and the non-translucent features will appear black. The substantially even illumination along the mandrel afforded by the light emitting member being disposed within the bore of the mandrel minimizes shadows adjacent the non-translucent features, thereby providing sharp contrast between the translucent and non-translucent portions of the graft device. The sharp contrast facilitates accuracy in other manufacturing or system processes, such as inspection, measurement, imaging, trimming and/or assembly processes. It may be desirable, for example, to trim and separate portions of the graft wall in close proximity to certain features or components of the graft device. Minimizing shadows cast on the graft wall around the stent due to light emitted through the graft wall results in a high contrast image which can, in turn, promote accuracy when trimming the graft wall along the stent.

In various embodiments, the support wall can be configured to be multi-axis, for example, for trimming grafts with side branches.

In various other embodiments, the lighted mandrel can be rotatably coupled to a base for rotation of the mandrel about a rotational axis that is fixed with respect to the base. The mandrel by this arrangement can rotate together with a medical device supported thereon to facilitate processing of the medical device. The mandrel can also be operatively coupled to an actuator, such as an electric motor, and to a controller to facilitate automated rotation of the mandrel based on data received by an imaging device and processed by the controller.

Example 1

Referring to FIGS. 2-6, in accordance with various embodiments, a lighted mandrel 100 was formed as follows. A transparent, smooth-surfaced quartz tube 140, serving as a support wall, was obtained from (Technical Glass Products, Painesville Twp., OH). The quartz tube 140 had the following dimensions: 4.13 mm outer diameter, 2.1 mm inner (luminal) diameter, and 160 mm length. A cold cathode fluorescent lamp (CCFL), 2.0 mm in diameter and 157 mm in length was obtained from (CC20157, CCFL Warehouse, Omaha, Nebr.) to function as the light emitting member 200. The CCFL was inserted into the lumen 130 of the quartz tube 140. A pair of electrodes for each end of the mandrel was fabricated of stainless steel. A first electrode 150 of the pair of electrodes was formed to have a generally pyramidal shape for engaging a mating output of an actuator. A second electrode 160 of the pair of electrodes was formed as a truncated cone or of generally frustoconically shape. Each electrode 150, 160 transitions toward a generally cylindrical base 152, 162 having an outside diameter slightly less than the inside diameter of the quartz tube 140. A through hole 154, 164 was formed through a longitudinal center of each of the electrodes 150, 160. The CCFL extended longitudinally between opposite ends of quartz tube 140 and had an electrical lead 156, 166 extending outwardly from each end. Each lead 156, 166 was inserted into the through hole 154, 164 of each electrode 150, 160 and held in place by friction fit. The cylindrical bases 152, 162 of the electrodes 150, 160 were inserted in opposite ends of the lumen 130 and fixedly secured to the quartz tube 140 with an adhesive.

Figure 3A:
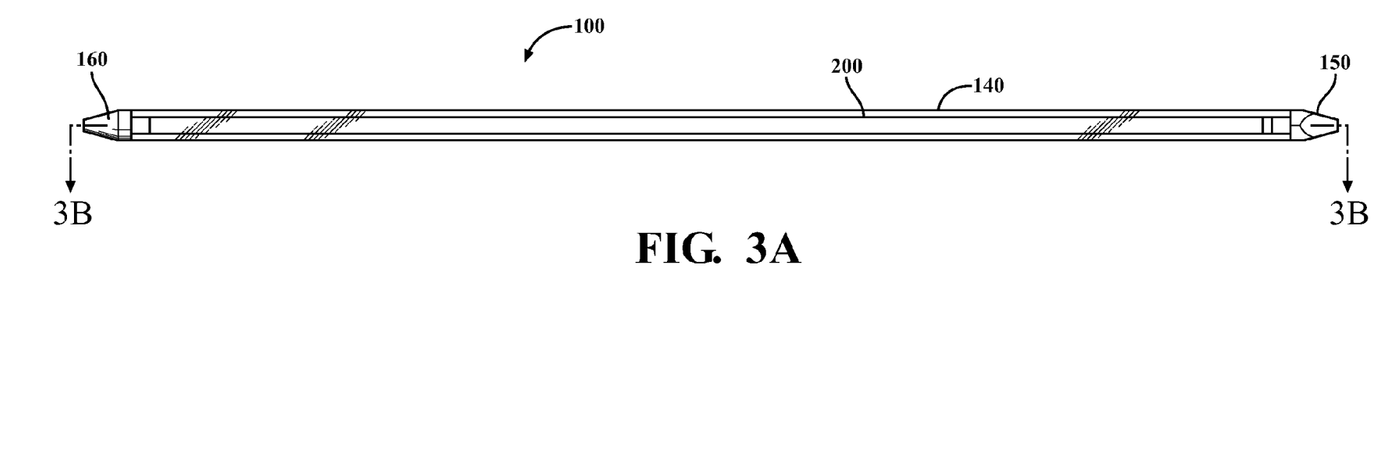
FIG. 3A is a front elevational view of the lighted mandrel of FIG. 2.
Figure 3B:
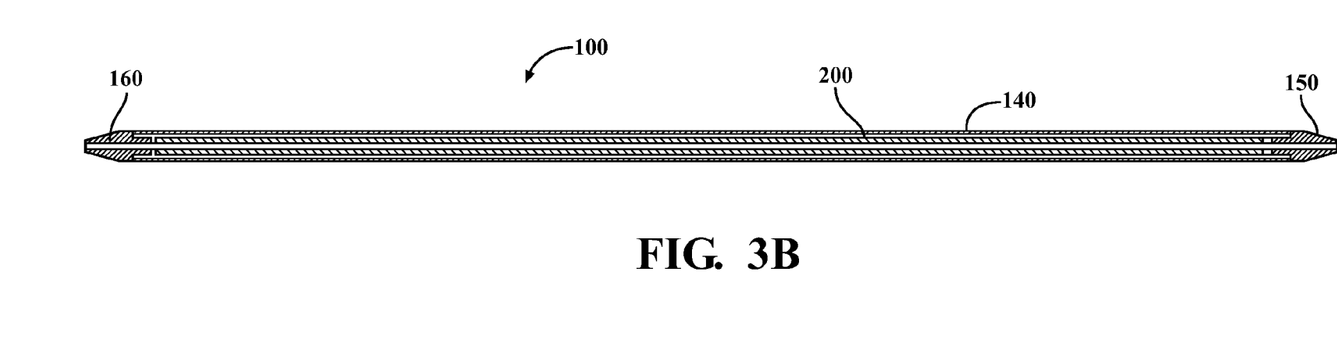
FIG. 3B is a cross sectional view of the lighted mandrel, as indicated in FIG. 3A.

The two electrical wire leads 156, 166 were then trimmed flush with the ends of the electrodes 150, 160. A longitudinal cross section of the assembled light source and source wall assembly is shown illustratively in FIG. 3B, showing a cross section taken at A-A in FIG. 3A.

Example 2

Figure 1A:
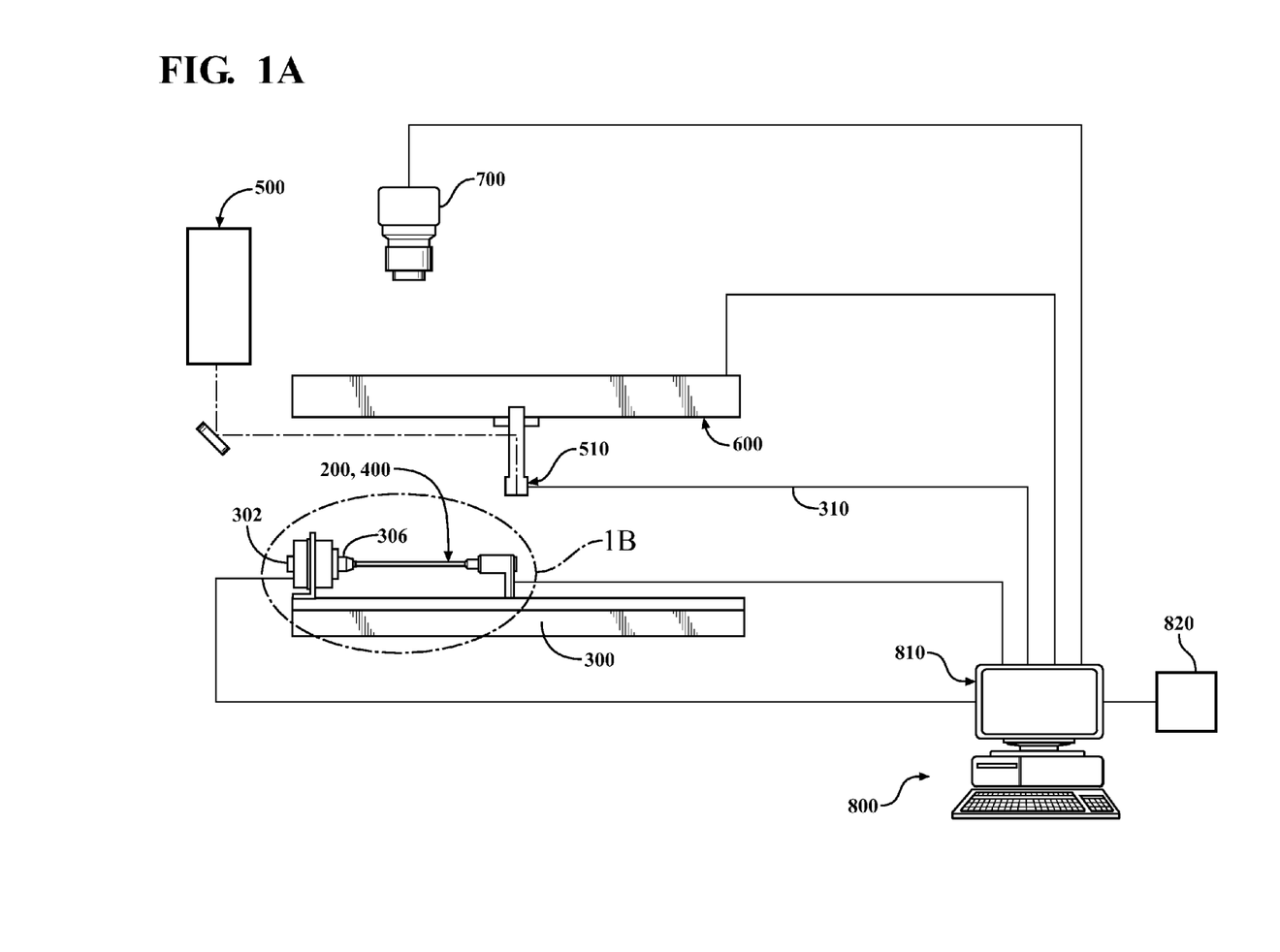
FIG. 1A is a schematic view of a medical device processing system.
Figure 1B:
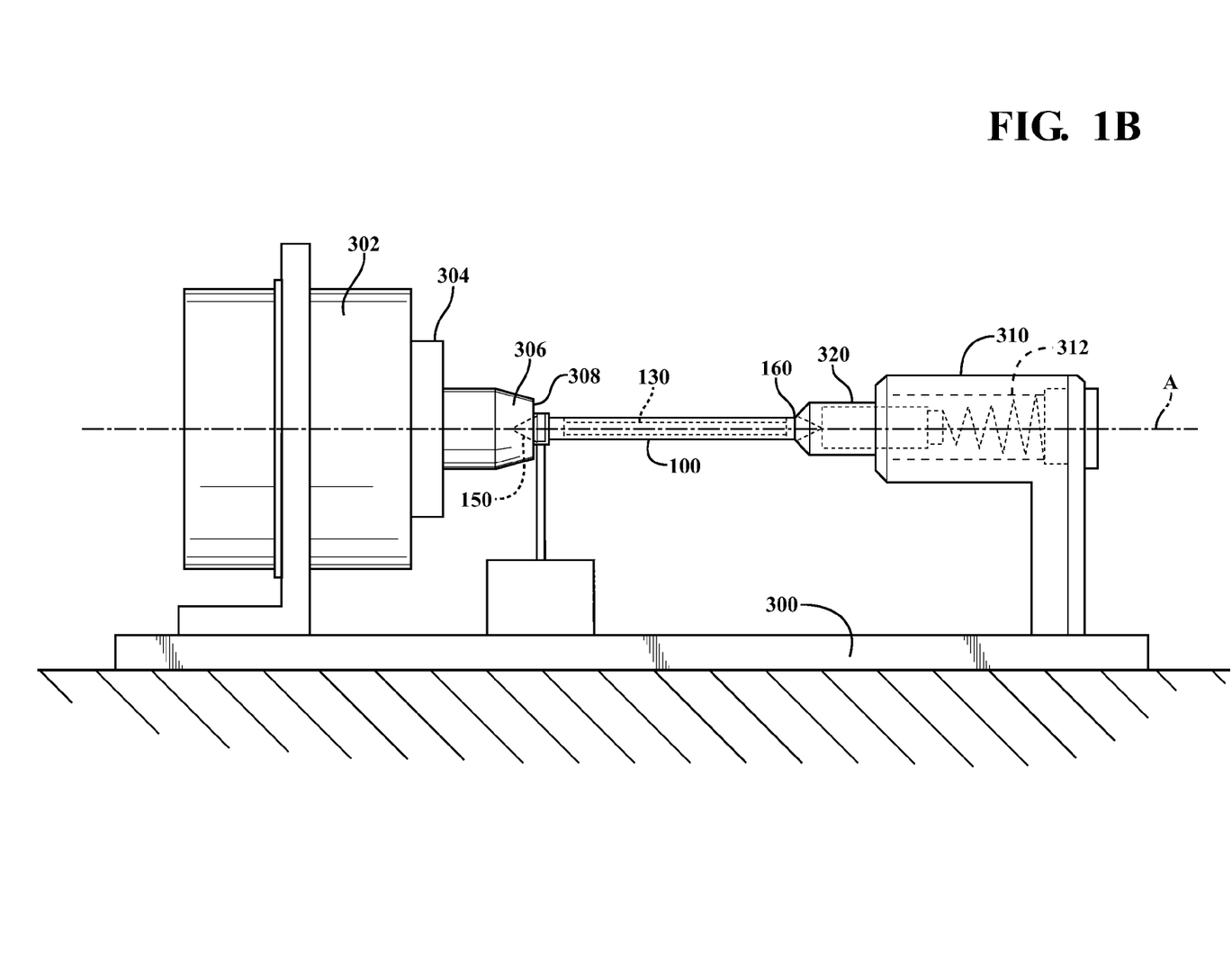
FIG. 1B is a schematic view of a medical device system having a spring actuated electrical contact for engaging one of the first and second electrode ends of the lighted mandrel and an electrically-isolated adapter for engaging the other of the first and second electrode ends of the lighted mandrel.

Referring to FIGS. 1A and 1B, the following components, along with the lighted mandrel, as described in Example 1, were assembled to form a medical device processing system 10, in accordance with various embodiments. A base or vertical stage 300 (ZP-200 series, Parker Hanlin Corp, Cleveland, Ohio); an actuator or rotary motor 302 (CM2650-25000, Emotec, Englewood, Colo.); a cutting device comprising a $CO_2$ laser 500 (C-30A, Coherent, Santa Clara, Calif.) and a laser focusing lens 510 (CM-2650-HHC-25K, II-VI Optics, Saxonburg, Pa.); a linear stage 600 (PLG 110 series, Primatics, Tangent, Oreg.); an imaging device or line scan camera 700 (P2-23-08K40, Teledyne DALSA, Waterloo, Ontario, Canada); a controller 800 comprising a computer (PC) 810 (T5400, Dell Computer, Round Rock, Tex.), a motion controller 820 (DMC-4040 series, Galil, Rocklin, Calif.), and vision processing software installed on the computer (VisionPro, Cognex Corp., Natick, Mass.).

Figure 2:
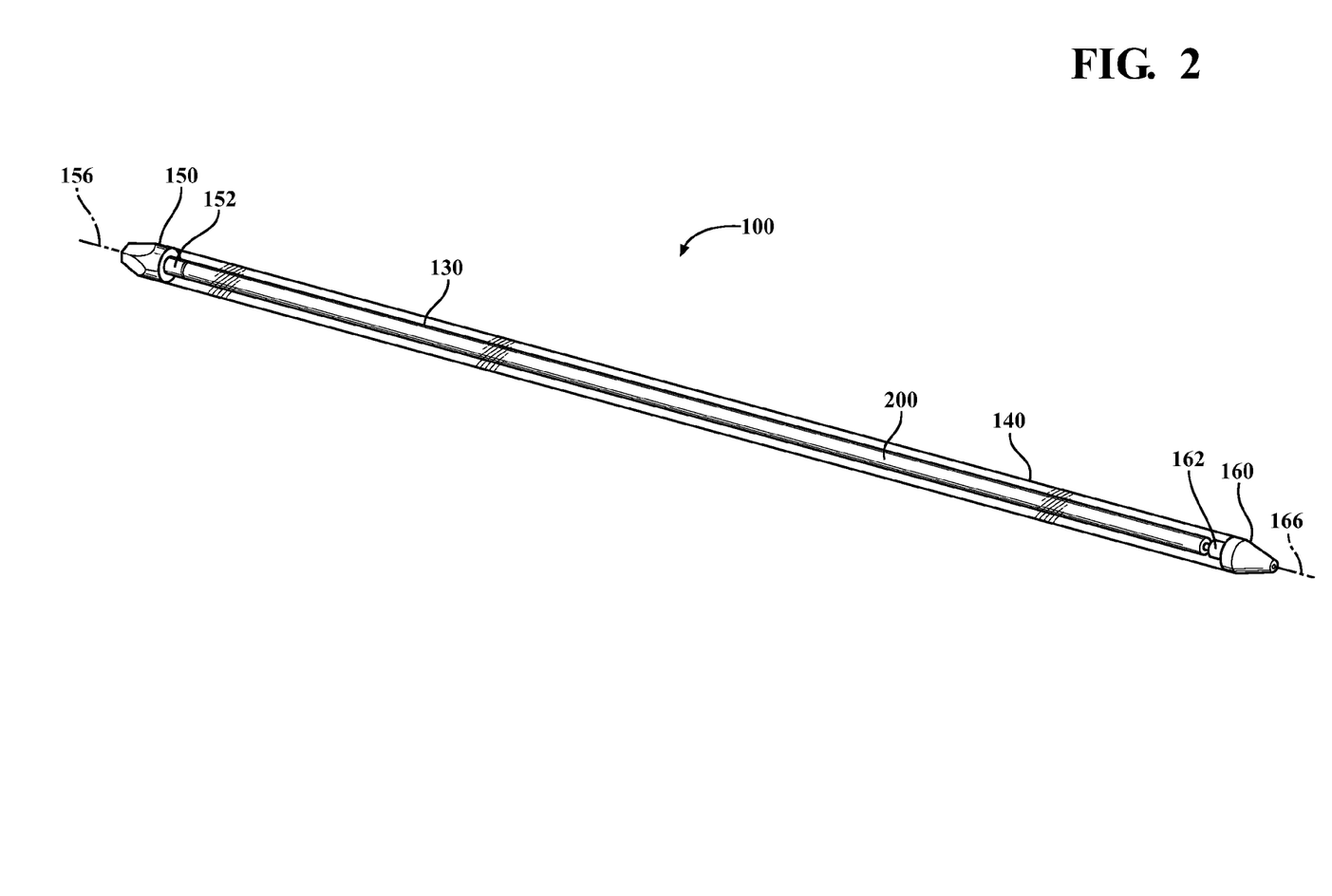
FIG. 2 is a perspective view of a lighted mandrel of the medical device processing system for supporting and illuminating a medical device.
Figure 5:
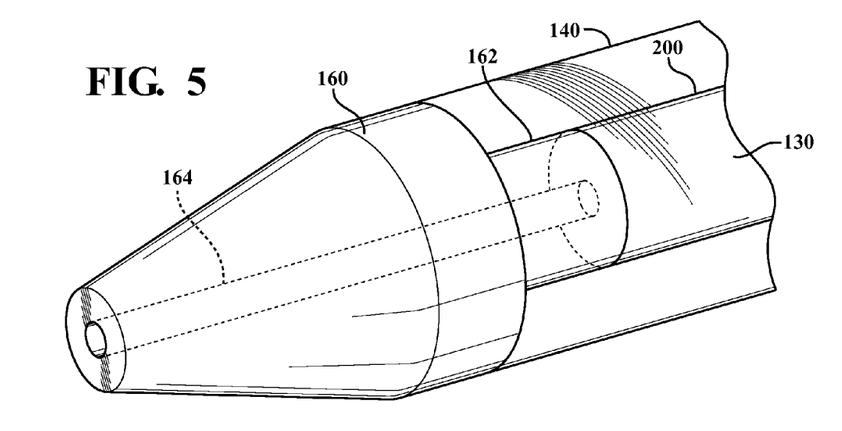
FIG. 5 is a first electrode end of the lighted mandrel.
Figure 6:
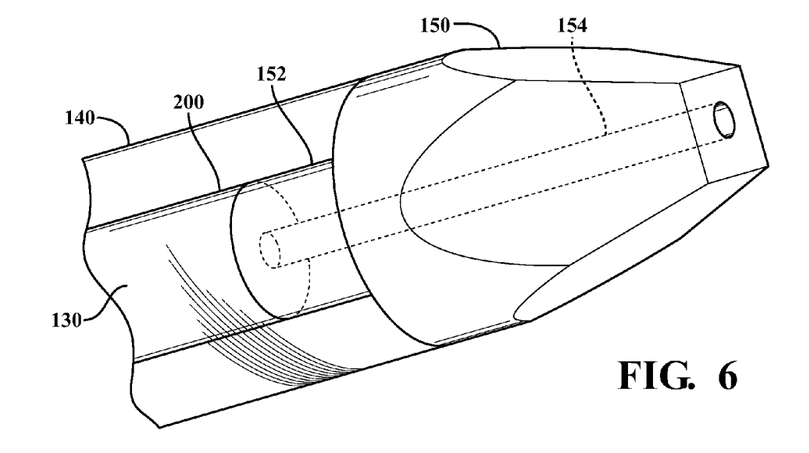
FIG. 6 is a second electrode end of the lighted mandrel.

An electrically isolated tailstock 310 for holding one end of the lighted mandrel 100 was fabricated and fixedly secured to the base. An opening 312 was formed in the tailstock 310 to support a spring actuated electrical contact 320 for matingly engaging the frustoconically-shaped second electrode 160, as shown in FIGS. 2-3 and 5. The spring actuated electrical contact 320 is axially displaceable generally along the rotational axis (indicated at "a" in FIG. 1B) and continuously spring biased toward the mandrel 100. The spring actuated electrical contact 320 was connected to an output of a CCFL inverter (not shown). The motor 302 was attached to the vertical stage 300 in line with the tailstock 310. An electrically-isolated adapter 306 was attached to an output drive shaft 304 of the rotary motor 302. The adapter 306 included a stainless steel electrical contact 308 shaped to matingly receive and engage the pyramidally shaped first electrode 150 of the mandrel 100, as shown in FIGS. 2-3 and 6. This contact 308 was connected to a second output of the CCFL inverter (not shown). The focusing lens 510 was attached to the linear stage 600 which was positioned over the vertical stage 300. The position of the focusing lens 510 was adjusted to focus a beam from the laser 500 approximately on a top of the outer surface of the lighted mandrel 100 and along its longitudinal centerline. The beam from laser 500 was directed to the focusing lens 510 via a flying optic system which included standard directional mirrors 502. The camera 700 was positioned so as to receive the image from the top of the outer surface of the mandrel 100 along its longitudinal centerline. The linear stage 600 allowed the laser 500 and beam emitted therefrom to be selectively positioned relative to the mandrel 100. The vertical stage 300 allows selective positioning of mandrel 100 relative to the laser 500 and the camera 700. A software program (not shown) was compiled for the computer 810 to control the camera 700 and the motion controller 820 (via data and power connections). Electrical and data connections were made between the motion controller 820 and each of the laser 500 (using a pulse width modulation output), rotary motor 302, the vertical stage 300, and the linear stage 600. The motion controller 820 also managed system inputs and outputs such as interlocks and switching the CCFL on and off.

Example 3

Using the medical device processing system in Example 2 and the lighted mandrel 100 in Example 1, a graft device was trimmed as follows.

Figure 4A:
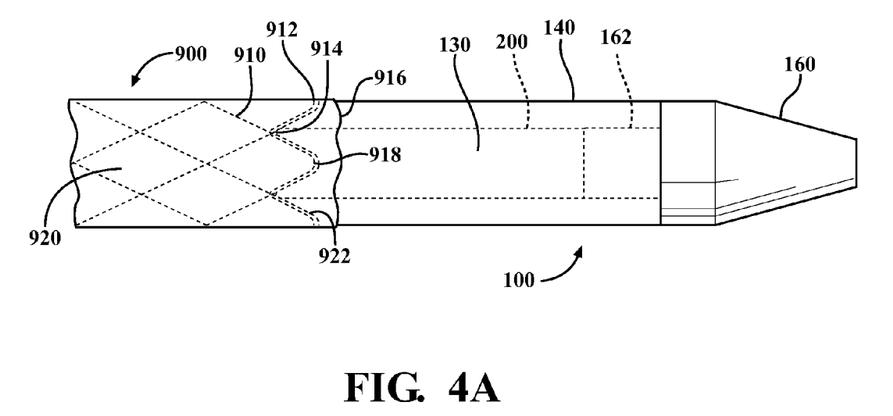
FIG. 4A is partial front elevational view of the lighted mandrel shown illustratively with an untrimmed graft device mounted thereon.

Referring to FIG. 4A, a graft device in the form of a stent-graft 900 was obtained having a graft wall 920 formed from layers of ePTFE film bonded together using fluoroethylene propylene (FEP) and a stainless steel support frame 910 interposed between the film layers. The support frame 910 had a generally diamond shaped configuration having peaks 912 and valleys 914. The stent-graft 900 had an inside diameter slightly larger than the outside diameter of the mandrel 100, as described in Example 1. An end 916 of the graft wall 920 is axially spaced apart from an end 918 of the support frame 910 defining an excess portion 924 of graft wall 920 there between.

The stent-graft 900 was slid over support surface of the lighted mandrel 100 and held in place by friction. The second electrode 160 was positioned within the spring actuated electrical contact 320 of the tailstock 310. While pressing the mandrel 100 toward the spring actuated electrical contact 320, the first electrode 150 at the opposite end of the mandrel 100 was positioned and engaged with the electrically-isolated adapter 306 attached to the rotary motor 302.

The computer 810 and all other electrical components of the processing system were powered up, including the CCFL inverter (not shown). The vertical stage 300 was moved such that the surface of the support wall was in focus with both imaging system 700 and beam of the laser 500. The CCFL 200 was allowed to come to a steady operating state.

The rotary motor 302 was activated to rotate the lighted mandrel 100. During rotation, line scan image frames of the stent-graft 900 were captured by the camera 700 and fed to the vision processing software for image acquisition. Upon completion of the image acquisition, the CCFL 200 was powered down. Image analysis was then performed by the computer 810 using the vision processing software.

Figure 4B:
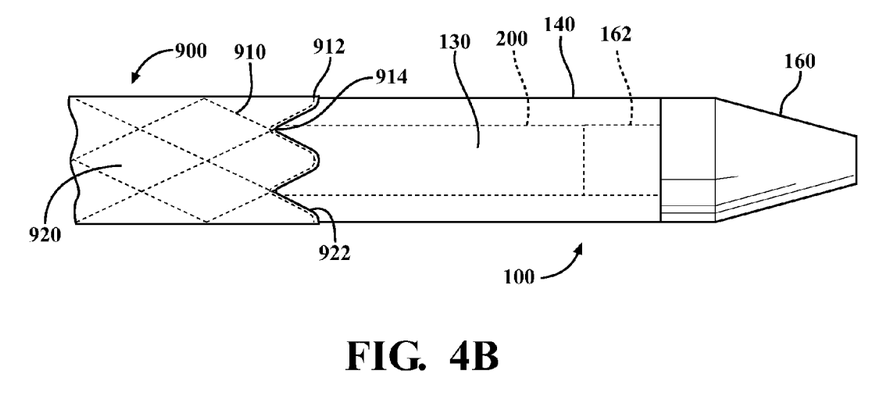
FIG. 4B is a partial front elevational view of the lighted mandrel shown illustratively with a trimmed graft device mounted thereon.

The results of the image analysis were used by the compiled software to computationally define a cut path 922 along the graft wall 920 adjacent the end of the support frame 910. The computed cut path was used by the motion controller 820 to move the linear stage 600 to direct the beam from the laser 500 for cutting along the cut path while the stent-graft 900 and mandrel 100 were rotated together about the longitudinal axis of the mandrel 100. The laser beam trimmed the graft wall 920 in close proximity to the support frame 910 and allowed removal of the excess portion 924 of the graft wall 920, as seen in FIG. 4B. The laser power required was determined empirically for the ePTFE material used to form the graft wall 920.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A graft device processing system, said graft device processing system comprising:
    a base;
    a tubular support wall having an outer surface for supporting thereon a generally tubular graft device and an inner surface defining a longitudinally extending lumen, the support wall being at least translucent to allow light from the light emitting member to pass therethrough; and
    a light emitting member disposed within the lumen for projecting light outwardly through the support wall and toward the graft device supported on the outer surface.

2. A graft device processing as set forth in claim 1, wherein the support wall is formed from quartz.

3. A graft device processing as set forth in claim 1, wherein the support wall is rotatably coupled to the base for rotation of the support wall and the light emitting member together about a rotational axis that is fixed with respect to the base.

4. A graft device processing system as set forth in claim 3, wherein at least one of the inner and outer surfaces of the support wall is polished.

5. A graft device processing system as set forth in claim 1 including a first electrode fixedly secured to an end of the support wall that is generally frustoconically shaped to facilitate installation and removal of the support wall from the base, and accommodate rotation of the support wall about the rotational axis.

6. A graft device processing system as set forth in claim 5 including a spring actuated electrical contact mounted to the base for engaging the first electrode, the spring actuated electrical contact being displaceable along the rotational axis to facilitate engagement and disengagement with the first electrode.

7. A graft device processing system as set forth in claim 5 including a rotary motor for rotating the support wall and light emitting member together about the rotational axis.

8. A graft device processing system as set forth in claim 7 including a second electrode having a generally pyramidal shape for matingly engaging an output shaft of the rotary motor.

9. A graft device processing system as set forth in claim 8 including a laser for trimming the medical device mounted on the support wall.

10. A graft device processing system as set forth in claim 9 including an imaging device for capturing image data of the medical device mounted on the support wall.

11. A graft device processing system as set forth in claim 10 including a controller operatively coupled to each of the rotary motor, laser and imaging device for automatic trimming of the medical device on the support wall based on imaging data received by the imaging device.

12. A graft device processing system as set forth in claim 1, wherein the light emitting member comprises a rod-shaped lamp.

13. A graft device processing system as set forth in claim 1, wherein the light emitting member comprises a phosphor coating along the inner surface of the support wall, the light emitting member further comprising a mercury vapor disposed within the lumen which can be energized to cause a release of light form the phoshor coating along the inner surface of the support wall.

14. A method of processing a tubular graft device, said method comprising:
   providing a graft device processing system having a base; a longitudinally extending light emitting member; a tubular support wall having an outer surface for supporting thereon a generally tubular graft device and an inner surface defining a longitudinally extending lumen for receiving the light emitting member therein, the support wall being at least translucent to allow light from the light emitting member to pass therethrough; wherein the support wall is rotatably coupled to the base for rotation of the support wall and the light emitting member together about a rotational axis that is fixed with respect to the base;
   placing and securing a graft device along the outer surface of the support wall;
   illuminating the graft device by activating the light emitting member; and
   rotating the support wall, light emitting member and the graft device supported on the outer surface of the support wall together about the rotational axis.

15. A method of processing a tubular graft device as set forth in claim 14 including:
   providing an imaging device for capturing image data of the graft device while illuminated by the light emitting member; and
   capturing imaging data.

16. A method of processing a tubular graft device as set forth in claim 15 including: providing a controller for receiving and processing image data from the imaging device.

17. A method of processing a tubular graft device as set forth in claim 16 including: providing a rotary motor for rotating the support wall and light emitting member together about the rotational axis.

18. A method of processing a tubular graft device as set forth in claim 17 including:
   providing a laser coupled to the controller;
   defining a cut path for the laser based on image data received by the controller from the imaging device; and
   cutting the graft device with the laser while rotating the graft device about the rotational axis.

19. A method of processing a tubular graft device as set forth in claim 18 including:
   providing electrodes on each end of the support wall to facilitate selective installation and removal of the support wall the base and accommodate rotation of the support wall and light emitting member together about the rotational axis relative to the base.

20. The method as set forth in claim 14 including providing the support wall with the outer surface having a larger outer peripheral dimension than the graft device such that the graft device retained along the outer surface of the support wall by friction.

21. A medical device processing system, said medical device processing system comprising:
   a support wall for supporting a medical device to be processed;
   a laser for cutting the object disposed along the support wall;
   an imaging device for capturing imaging data;
   a controller operatively coupled to each of the laser and imaging device for processing the captured imaging data and controlling the cutting of the object by the laser based on processed captured imaging data; and
   a light source,
   wherein the support wall is optically transmissive to allow light from the light source to pass therethrough and illuminate the object while the imaging system captures imaging data.

22. A medical device processing system as set forth in claim 21, wherein the support wall is generally tubular and has a generally cylindrical outer surface for supporting thereon a generally tubular graft.

23. A medical device processing system as set forth in claim 22, wherein the support wall includes a generally cylindrical inner surface defining a longitudinally extending lumen for receiving the light emitting member therein.

* * * * *